US010478316B2

(12) United States Patent
Greter et al.

(10) Patent No.: US 10,478,316 B2
(45) Date of Patent: Nov. 19, 2019

(54) DISCHARGE DEVICE FOR BONE REPLACEMENT MATERIALS

(71) Applicant: MEDMIX SYSTEMS AG, Rotkreuz (CH)

(72) Inventors: Andy Greter, Minusio (CH); Benjamin Nieber, Eschenbach (CH); Philip Procter, Divonne les Bains (FR)

(73) Assignee: Sulzer Mixpac AG, Haag (Rheintal) (CH)

( * ) Notice: Subject to any disclaimer, the term of this patent is extended or adjusted under 35 U.S.C. 154(b) by 234 days.

(21) Appl. No.: 15/533,392

(22) PCT Filed: Dec. 17, 2014

(86) PCT No.: PCT/EP2014/078253
§ 371 (c)(1),
(2) Date: Jun. 6, 2017

(87) PCT Pub. No.: WO2016/095989
PCT Pub. Date: Jun. 23, 2016

(65) Prior Publication Data
US 2017/0340455 A1 Nov. 30, 2017

(51) Int. Cl.
*A61F 2/46* (2006.01)
*A61B 17/56* (2006.01)
(Continued)

(52) U.S. Cl.
CPC ............ *A61F 2/4601* (2013.01); *A61B 17/56* (2013.01); *A61B 17/7095* (2013.01);
(Continued)

(58) Field of Classification Search
CPC ..................... A61F 2/4601; A61B 17/320016
See application file for complete search history.

(56) References Cited

U.S. PATENT DOCUMENTS 4,784,607 A   11/1988 Francois
5,697,903 A   12/1997 Fischer
(Continued)

FOREIGN PATENT DOCUMENTS

CH          708 198 A1    12/2014
CN         203954428    * 11/2014
(Continued)

OTHER PUBLICATIONS

Communication dated Aug. 3, 2018 from the State Intellectual Property Office of the P.R.C. in counterpart application No. 201480084216.9.
(Continued)

*Primary Examiner* — Christian A Sevilla
(74) *Attorney, Agent, or Firm* — Sughrue Mion, PLLC

(57) ABSTRACT

A discharge device (1) comprising a housing (200), a container insert (300) rotatably arranged therein and a piston. A lateral cutout (205) is formed in one housing wall (204), and a lateral container opening (303) is formed in one container wall (304). In order to prevent the compound from being compressed as the compound is discharged, the lateral container opening extends continuously as far as the distal container end (302) without a region of the container wall adjoining the lateral container opening in the distal direction along the longitudinal axis. In order to make it easier to put in the compound, the wall thickness of the housing wall decreases continuously toward the lateral cutout (205). In order to prevent clogging of the piston, the cross section of the container insert widens continuously in the distal direction.

24 Claims, 13 Drawing Sheets

(51) Int. Cl.
  *A61F 2/28* (2006.01)
  *A61B 17/70* (2006.01)
  *A61B 17/88* (2006.01)
  *A61F 2/30* (2006.01)

(52) U.S. Cl.
  CPC ...... *A61B 17/8811* (2013.01); *A61B 17/8816* (2013.01); *A61B 17/8822* (2013.01); *A61B 17/8825* (2013.01); *A61B 17/8833* (2013.01); *A61F 2/28* (2013.01); *A61B 2017/8813* (2013.01); *A61F 2002/3037* (2013.01); *A61L 2430/02* (2013.01)

(56) References Cited

U.S. PATENT DOCUMENTS

| | | | |
|---|---|---|---|
| 6,309,372 | B1 | 10/2001 | Fischer et al. |
| 6,582,438 | B2 | 6/2003 | Demayo |
| 8,034,034 | B2 | 10/2011 | Hess et al. |
| 2010/0121268 | A1 | 5/2010 | Keller |
| 2014/0303744 | A1 | 10/2014 | Evans et al. |

FOREIGN PATENT DOCUMENTS

| | | |
|---|---|---|
| CN | 203954428 U | 11/2014 |
| EP | 2 774 583 A1 | 9/2014 |
| WO | 9421313 A1 | 9/1994 |
| WO | 0045854 A2 | 8/2000 |
| WO | 2008/014622 A1 | 2/2008 |

OTHER PUBLICATIONS

International Search Report of PCT/EP2014/078253 dated Oct. 19, 2015 [PCT/ISA/210].
International Preliminary Report on Patentability and translation of Written Opinion dated Jun. 29, 2017, issued by the International Bureau in corresponding International Application No. PCT/EP2014/078253.

\* cited by examiner

B-B

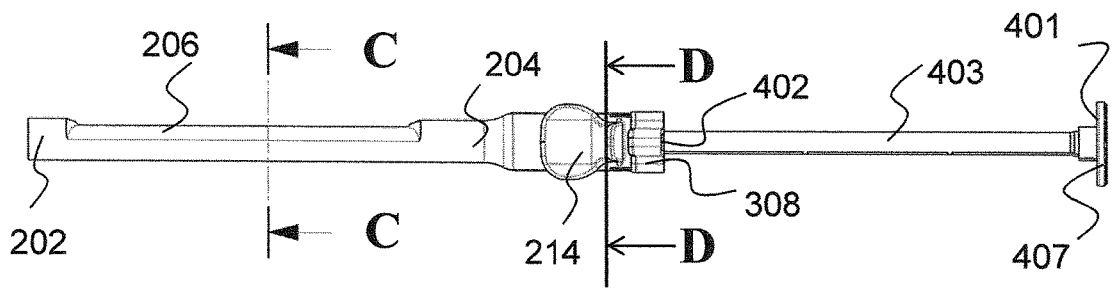
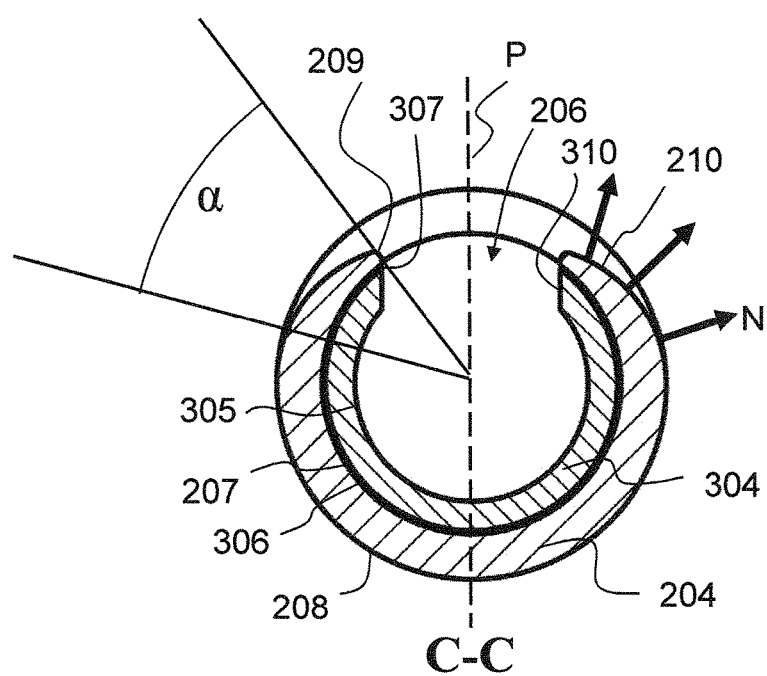
FIG. 10
FIG. 11
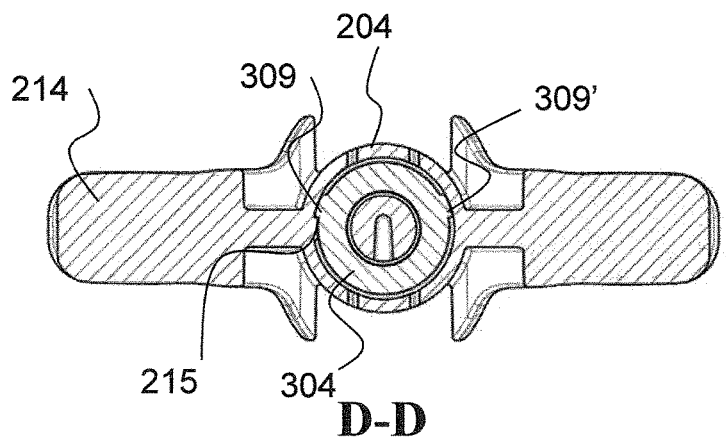
FIG. 12

DISCHARGE DEVICE FOR BONE REPLACEMENT MATERIALS

CROSS REFERENCE TO RELATED APPLICATIONS

This application is a National Stage of International Application No. PCT/EP2014/078253, filed Dec. 17, 2014, the contents of which are incorporated herein by reference in its entirety.

TECHNICAL FIELD

The present invention relates to a discharge device for discharging a poorly flowable mass, in particular a bone replacement material (bone graft material), comprising a housing and a container insert situated therein, wherein a lateral cutout is formed in a housing wall of the housing, wherein a lateral container opening is formed in a container wall of the container insert, and wherein the container insert can be rotated relative to the housing between a closed position, in which the housing wall closes the lateral container opening, and a release position, in which the lateral cutout releases the lateral container opening.

PRIOR ART

Bone replacement materials (bone graft materials) are utilized in various medical fields such as dentistry, orthopedics, or reconstructive surgery. Bone replacement materials can be subdivided into so-called autografts (bone transplant produced from a patient's own bone material), allografts (bone transplant produced from human bone material foreign to the patient, e.g., obtained from a bone bank), xenografts (from biological material of non-human origin), and synthetic bone replacement materials (e.g., on the basis of hydroxyapatite, frequently containing admixtures of growth factors and endogenous substances).

In certain applications, the bone replacement material is present in the form of a poorly flowable mass. This mass usually consists of a particulate or granular solid phase (e.g., ground or otherwise pulverized, solid bone components and/or powdery synthetic materials such as hydroxyapatite, tricalcium phosphate, calcium sulfate, or bioglass) and a liquid phase (e.g., endogenous blood, blood plasma, aspirated bone marrow, etc.). The consistency of such a mass often resembles moist sand. In addition, relatively large particles such as, for example, bone fragments, can be present in the mass. Such a mass, when compressed, tends to agglomerate and nearly entirely loses its flowability. Depending on the consistency and the liquid content, the mass can have a rather powdery or rather pasty consistency. Said mass cannot be injected using conventional injection devices.

The handling and the administration of such a mass at its intended site can be associated with some difficulties. Traditionally, the mass is applied by the surgeon at the intended site manually or with the aid of a spatula. Depending on the position of the intended site, this can be difficult to impossible, however. There is a need, therefore, to bring masses of the type mentioned herein to their intended site, which can lie inside the body, in particular, with the aid of syringe-like discharge devices. As mentioned above, the mass can be a bone replacement material, although said mass can also be another type of material which is intended to be introduced into the interior of a human or animal body.

Various discharge devices have been proposed for this purpose in the prior art. Various methods for filling such a discharge device with a mass have also been proposed. Both the filling as well as the subsequent administration can be difficult, however, due to the special consistency of a mass of the aforementioned type.

U.S. Pat. No. 8,034,034 B2 discloses a syringe having a lateral opening. Injectable material such as, for example, bone cement, can be filled into the syringe through the opening. After the filling has been completed, the opening is closed by means of a cover. Multiple possibilities for closing the opening are disclosed; for example, the cover can slide over the opening, e.g., upon actuation of the syringe piston, or said cover is swiveled over the opening upon actuation of the syringe piston. It is also disclosed to close the opening independently of an actuation of the syringe piston. Such a syringe is poorly suitable, however, for discharging bone replacement materials having a consistency containing a large amount of particulate matter. In practice, the counterpressure by the bone replacement material can become so great that it becomes completely impossible to discharge the material.

U.S. Pat. No. 6,582,438 discloses a discharge device which comprises two concentric cylinders having elongate openings in their side walls, and a piston. In order to fill a bone replacement material into the cylinder, the cylinders are rotated opposite one another in such a way that their openings come to lie one above the other. The bone replacement material is then filled laterally. After the filling has been completed, the outer cylinder is rotated, and therefore it closes the opening of the inner cylinder, which is lying below it, by means of its lateral wall. The bone replacement material is discharged by way of the piston being pushed through the inner cylinder. In the case of this discharge device as well, it is shown in practice, however, that the discharge of bone replacement materials containing large amounts of particulate matter can be associated with a very high counterpressure, up to the point of a complete blockage of the piston. The cause therefor was unknown up to now.

In addition, relatively large particles in the material to be discharged, such as, for example, bone fragments, can result in the case, even during filling, in which the lateral opening can no longer be correctly closed, and, during discharge, such particles can additionally result in a blockage of the piston.

SUMMARY OF THE INVENTION

In a first aspect, it is an object of the present invention to provide a discharge device for discharging a poorly flowable mass, in particular a bone replacement material, which makes it possible to discharge the mass from the device with a reduced amount of force.

A discharge device for discharging a mass is therefore provided, which comprises:

a housing having a peripheral housing wall, an open proximal housing end, and an open distal housing end, wherein a lateral cutout is formed in the housing wall; and a container insert, which is situated in the housing and comprises a peripheral container wall, an open proximal container end, and a distal container end, wherein a lateral container opening is formed in the container wall, and wherein the container insert can be rotated about a longitudinal axis relative to the housing between a closed position, in which the housing wall closes the lateral container opening, and a release position, in which the lateral cutout releases the lateral container opening.

According to the invention, the lateral container opening extends continuously in the axial direction up to the distal container end without a region of the container wall adjoining the lateral container opening in the distal direction along the longitudinal axis.

In the case of the devices in the prior art, it was not understood for a long time why these devices build up a very high counterpressure, up to the point of complete blockage, when used with bone replacement materials or similar masses. In the present invention, it was recognized that this has to do with the special, sand-like consistency of such masses. Due to this consistency, even the slightest tapers result in a compression of the material and, therefore, to an agglomeration, which makes the continued discharge much more difficult or even completely prevents the continued discharge. Due to the simple measure of omitting a wall region at the distal end of the container opening, a tapering of the cross-section of the container insert can be avoided, and the discharging process is made very substantially easier.

Preferably, the hollow space defined by the container and the housing has a cross-section overall which does not reduce anywhere, at least between the proximal end of the container opening and the distal container end.

In the following, directional information is utilized as follows. The container insert, which is rotatably situated in the housing, defines a central longitudinal axis which coincides with the rotational axis of the rotary motion. The distal direction is the direction in which the mass is advanced along the central longitudinal axis toward the housing outlet opening in order to be discharged. The proximal direction refers to the direction opposite thereto. The lateral direction refers to a radial direction with respect to the longitudinal axis.

In a second aspect, it is an object of the present invention to provide a discharge device for discharging a mass, in particular a bone replacement material, which makes it easier to perform filling with the mass.

A discharge device for discharging a mass is therefore provided, which comprises:

a housing having a peripheral housing wall, an open proximal housing end, and an open distal housing end, wherein a lateral cutout is formed in the housing wall; and a container insert, which is situated in the housing and comprises a peripheral container wall, an open proximal container end, and a distal container end, wherein a lateral container opening is formed in the container wall, and wherein the container insert can be rotated about a longitudinal axis relative to the housing between a closed position, in which the housing wall closes the lateral container opening, and a release position, in which the lateral cutout releases the lateral container opening.

In the region of the lateral cutout, the housing wall has a wall thickness (measured in the radial direction) which continuously decreases in the circumferential direction toward the lateral cutout through an angular range of at least 10°.

When the container insert is filled with a mass, e.g., with a bone replacement material, or with a component of such a mass, through the lateral cutout and through the lateral container opening, excess mass can thereby be easily wiped away in the circumferential direction, on the one hand, without hindrance by the housing wall, and, on the other hand, a sufficiently great stability of the housing wall is still ensured.

The decrease in the radial wall thickness preferably takes place in this case only on the outer side of the housing wall (i.e., on the outer lateral face of the housing). This preferably takes place in such a way that the housing wall forms a blade-like scraping edge at the boundary of the lateral cutout. The outer lateral face of the housing and the inner outer lateral face of the housing extend toward one another, toward the scraping edge, at an acute angle in this case, preferably at an angle of at least 5° and at most 60°, more preferably at least 10° and at most 45°. The scraping edge can be rounded in order to minimize the risk of injury.

The angular range across which the wall thickness decreases is preferably at least 20°, more preferably at least 30°, in the circumferential direction.

A gradual, continuous decrease of the radial wall thickness toward the lateral cutout or toward the scraping edge ensures that the housing wall curves outwardly away from the scraping edge in such a way that the normal vector on the outer lateral face of the housing adjoining the scraping edge does not have a directional component anywhere that extends in the direction of a radial plane extending centrally through the lateral cutout. In this way, an undesired funnel effect, which would make it difficult to wipe off the excess mass, is avoided during filling.

The lateral opening preferably comprises two boundaries which extend in parallel to one another and in parallel to the longitudinal axis. The scraping edge extends parallel to the longitudinal axis in this case.

The container wall can also have a radial wall thickness which decreases toward the lateral container opening in the circumferential direction, i.e., said container wall can taper toward the lateral container opening in the circumferential direction. Preferably, the wall thickness of the container wall decreases only on the inside, i.e., on the inner lateral face of the container. Preferably, the container wall thereby forms a blade-like shearing edge adjacent to the housing wall, said edge being adjoined by a shearing surface which is formed by a part of the inner lateral face of the container. The outer lateral face of the container and the inner lateral face of the container extend toward one another, toward the shearing edge, at an acute angle in this case, preferably at an angle of at least 5° and at most 60°, more preferably at least 10° and at most 45°. The scraping edge and the shearing edge preferably adjoin one another in the release position, i.e., together they form a type of blade, across which the mass to be filled can be wiped off.

In a third aspect, it is an object of the present invention to provide a discharge device for discharging a mass, in particular a bone replacement material, in which a blockage of the piston by relatively large particles such as bone fragments during the discharge of the mass is avoided.

A discharge device for discharging a mass is therefore provided, which comprises:

a housing having a peripheral housing wall, an open proximal housing end, and an open distal housing end, wherein a lateral cutout is formed in the housing wall; and a container insert, which is situated in the housing and comprises a peripheral container wall, an open proximal container end, and a distal container end, wherein a lateral container opening is formed in the container wall, and wherein the container insert can be rotated about a longitudinal axis relative to the housing between a closed position, in which the housing wall closes the lateral container opening, and a release position, in which the lateral cutout releases the lateral container opening.

In order to prevent a piston from becoming jammed by relatively large particles such as bone fragments as said piston is being pushed through the container, the container insert has an open container cross-section which continuously and preferably linearly increases in the distal direction along the longitudinal axis across an axial range.

The continuous increase in the open container cross-section takes place in this case preferably by an amount which is calculated as follows: In the case of a container that has rotational symmetry on the inside, the internal diameter per unit of length increases by at least 0.5 per thousand, i.e., the internal diameter increases by at least 5 micrometers per centimeter of length of the container. Preferably, the increase is at least 2 per thousand. Preferably, on the other hand, the increase is at most 30 per thousand, i.e., the internal diameter increases by at most 0.3 millimeter for each centimeter of length of the container.

In the more general case of a container that is not necessarily rotationally symmetrical on the inside, a variable (D) per unit of length therefore increases by at least 0.5 per thousand, preferably by at least 2 per thousand, and at most 30 per thousand, wherein the variable (D) refers to a mean diameter and is defined as follows:

$$(D) = 2\sqrt{A/\pi},$$

wherein A refers to the open cross-sectional area of the container.

The axial range, across which the open container cross-section increases, preferably extends across a substantial portion of the length of the container. Specifically, it is preferred when this axial range extends continuously from the proximal end of the container opening up to the distal container end, i.e., when the gradual increase takes place across the entire length of the container opening. It can also suffice, however, when the gradual increase takes place across a portion of this length, e.g., across the distal 50% of the length of the container opening.

If the container opening has a length of 130 mm, for example, it is preferred that the mean diameter (D) increases continuously across this length by approximately 0.1 mm to 3 mm. If a rigid piston is used, the increase is preferably approximately 0.1 mm to 0.5 mm, particularly preferably approximately 0.3 mm, based on a length of 130 mm. If a piston is used that is capable of expanding radially (e.g., a longitudinally slotted piston of the type described in greater detail in the following), the increase is preferably approximately 0.5 mm to 3 mm, particularly preferably approximately 1 mm, based on a length of 130 mm.

All three aspects of the invention can be implemented independently of each other or can be arbitrarily combined with one another. The following considerations apply for all three aspects of the invention.

The outer side of the container wall preferably rests against the inner side of the housing wall and slides on the inner side of the housing wall during rotation of the container insert. The housing wall preferably has a cylindrical shape on the inside, in the region of the lateral cutout, and the container wall preferably has a corresponding cylindrical shape on the outside, in the region of the lateral container opening. Other rotationally symmetrical shapes are also possible, however.

Preferably, the discharge device also comprises a piston which is displaceable in the container insert along the longitudinal axis. Such a piston can also be optionally provided by an external ejecting device and therefore must not necessarily belong to the actual discharge device.

The piston preferably does not sealingly cooperate with the container wall. Said piston is preferably not made of an elastomer, but rather of a relatively hard material which does not produce a sealing effect with the container wall. It is also conceivable, however, that the piston comprises a soft material, in particular an elastomer, and/or that the piston is slotted. In particular, the piston can be slotted in such a way that said piston is capable of expanding radially. For example, the piston can comprise one slot or multiple slots which extend partially through the piston in parallel or diagonally to the longitudinal axis. The slots preferably form indentations which are open in the distal direction. Preferably, the piston comprises two slots which are open in the distal direction and which extend completely through the piston in the radial direction and intersect one another, in particular being positioned perpendicularly to one another in a radial plane. By means of the slots, the piston is subdivided into multiple segments which are radially elastically connected to the push rod. Upon application of a compression force from the outside, these segments give way radially inwardly and thereby reduce the outer circumference of the piston. When the compression force subsides, the segments spring back outwardly again. A piston comprising one or several such slots is therefore capable of expanding radially and of being radially compressed.

Such a capability to expand radially can be desirable, for example, during a continuous increase in the open container cross-section or the inner container diameter along the distal direction, since the piston should then have a smaller radial expansion in the region of a smaller inner container diameter than in a region of a larger inner container diameter. A piston made of a soft material would increasingly expand as the inner container diameter increases, and a piston comprising slots would increasingly spread apart as the inner container diameter increases.

The piston can be connected to a push rod in order to form a plunger. In this case, it is preferred when the piston radially extends slightly beyond the push rod, i.e., when the piston defines a piston diameter, the push rod defines a rod diameter, and the piston diameter is larger than the rod diameter. As a result, it is ensured that material such as, e.g., bone fragments, which pass by the piston and enter the region of the push rod, are prevented from blocking the push rod. The piston diameter is preferably larger than the rod diameter by at least 0.2 mm, in particular by at least 0.5 mm. Expressed in relative values, the rod diameter is preferably at most 95% of the piston diameter.

The housing, the container insert, the piston, and/or the push rod are preferably produced at least partially from plastic. Many plastics are largely transparent to X-ray radiation. In order to make it possible for the positioning of the discharge device in the patient's body to be nevertheless checked in the X-ray image or in CT, the housing, the container insert, the piston, and/or the push rod can comprise at least one radiopaque functional element. Said element can be situated, in particular, on the distal housing end, on the distal container end, and/or on the distal end of the piston. In particular, such a functional element can be embedded in the housing, the container insert, the piston, and/or the push rod. Said functional element can be an element made of metal or of a highly X-ray absorbent plastic or composite material. For example, the functional element can be installed annularly around the distal housing end, the distal container end, or the piston.

A deflector can be formed on the distal housing end, which adjoins the distal container end in the distal direction and is curved along the distal direction toward the central longitudinal axis. Such a curved deflector provides for a targeted discharge of the mass to be discharged toward one side.

In order to facilitate a rotation of the container insert in the housing, a radially protruding handle, e.g., in the form of two grip wings, can be formed on the proximal housing end, and a radially protruding twist handle can be formed on the open proximal container end.

At least one container rotation stop can be formed on the container insert, and at least one housing rotation stop can be formed on the housing, wherein the container rotation stop is formed so as to be contradirectional to the housing rotation stop, and wherein the container rotation stop and the housing rotation stop strike one another during a rotation of the container insert in the housing in the direction of the release position and/or during an opposing rotation in the direction of the closed position.

Preferably, the container rotation stop is designed as a cam or a stud on the outer circumference of the container insert, and the housing rotation stop is designed as a complementary cam or stud on the inner circumference of the housing.

The push rod can comprise a rod stop in the region of the distal rod end, and the open proximal container end can have a container stop which is complementary thereto, wherein, during a displacement of the rod along the proximal direction, the rod stop strikes the container stop in such a way that a complete removal of the rod from the container insert is prevented.

Preferably, the rod stop is designed in this case as an annular ridge around the push rod, and the container stop is designed as an inwardly directed detent projection or as an inner ridge on the inner circumference of the container.

The container insert can be prefilled with the mass, and a removable closure can close the housing outlet opening. The closure is preferably designed as a closure cap which is slid onto the distal housing end or is screwed thereon.

One first possible method of providing a mass to be discharged, in particular a bone replacement material, in a discharge device of the above-described type comprises the following steps of: i) rotating the container insert relative to the housing about the longitudinal axis, such that the lateral cutout releases the lateral container opening; ii) filling the mass to be discharged through the lateral cutout and through the lateral container opening into the container insert; and iii) rotating the container insert relative to the housing about the longitudinal axis, such that the housing wall closes the lateral container opening.

In a second possible method of providing a mass to be discharged, in particular a bone replacement material, in a discharge device of the above-described type, the container insert is prefilled with a first component of the mass, and the housing outlet opening is closed by a closure. The method then comprises the following steps of: i) rotating the container insert relative to the housing about the longitudinal axis, such that the lateral cutout releases the lateral container opening; ii) adding a second, preferably liquid component of the mass through the lateral cutout and through the lateral container opening to the first component; iii) rotating the container insert relative to the housing about the longitudinal axis, such that the housing wall closes the lateral container opening; and iv) removing the closure.

The discharge device described here can be used with ejection devices known per se. For example, WO 2013/063706 discloses an ejection device designed as a pistol dispenser comprising an adapter, wherein a fastening structure is formed on the adapter for attaching a container having a mass to be discharged. Given that the adapter and the proximal end of the discharge device proposed here are designed to be complementary to one another, the discharge device proposed here can be readily used with an ejection device of the type disclosed in WO 2013/063706.

BRIEF DESCRIPTION OF THE DRAWINGS

Preferred embodiments of the invention are described in the following with reference to the drawings which are intended merely for the purpose of explanation and are not intended to be interpreted to be limiting. In the drawings:

FIG. 10 shows a side view of the discharge device from FIG. 9;

FIG. 11 shows a cross-section through the discharge device from FIG. 10 in the plane C-C from FIG. 10;

FIG. 12 shows a cross-section through the discharge device from FIG. 10 in the plane D-D from FIG. 10;

DESCRIPTION OF PREFERRED EMBODIMENTS

Figure 1:
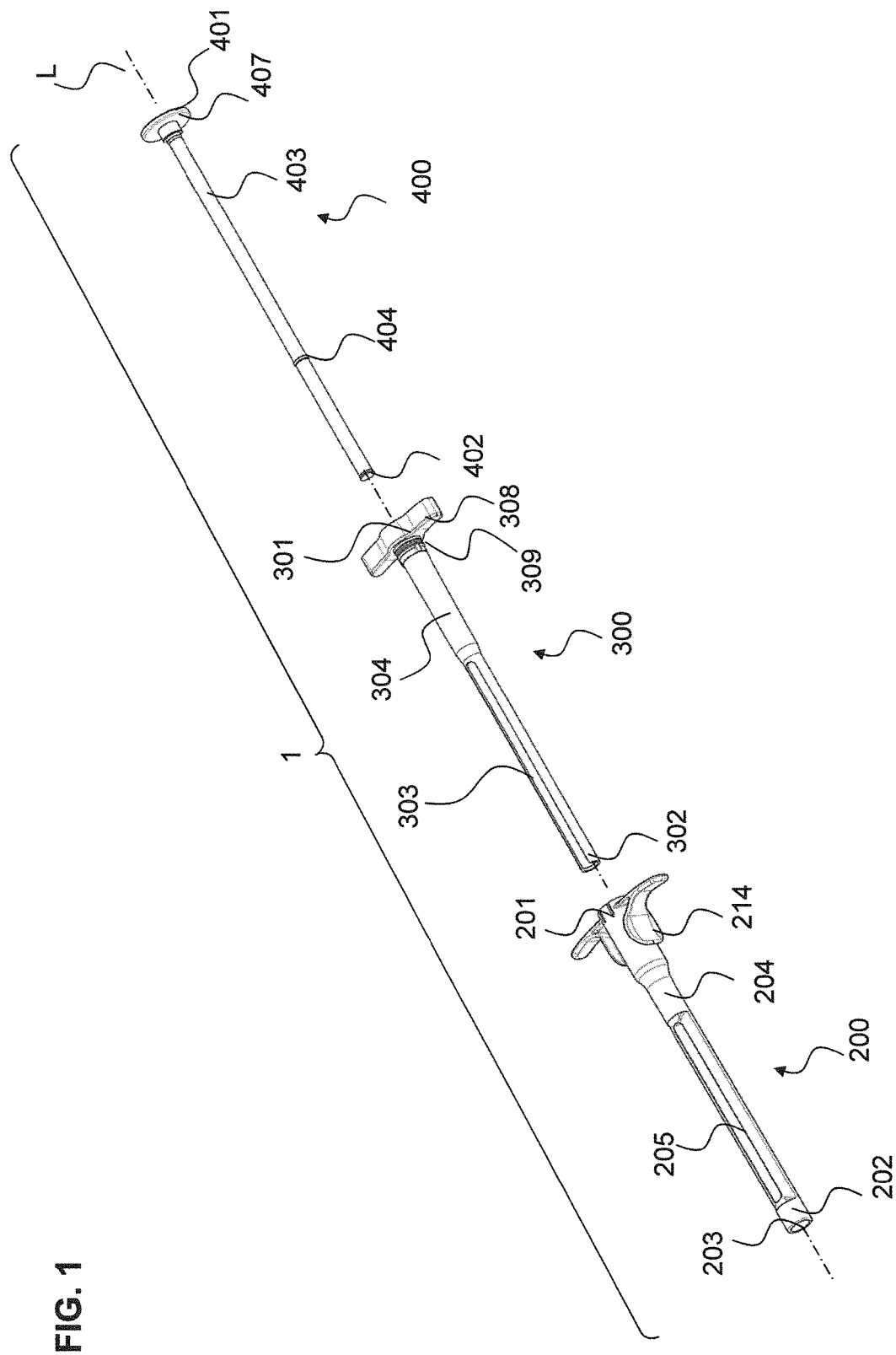
FIG. 1 shows a perspective exploded representation of one first exemplary embodiment of a discharge device comprising a housing, a container insert, and a rod.

A first embodiment of a discharge device for discharging a poorly flowable mass, e.g., a bone replacement material, is illustrated in FIGS. 1-20. As is evident from FIG. 1, the discharge device 1 comprises a housing 200, a container insert 300, and a rod 400.

Figure 2:
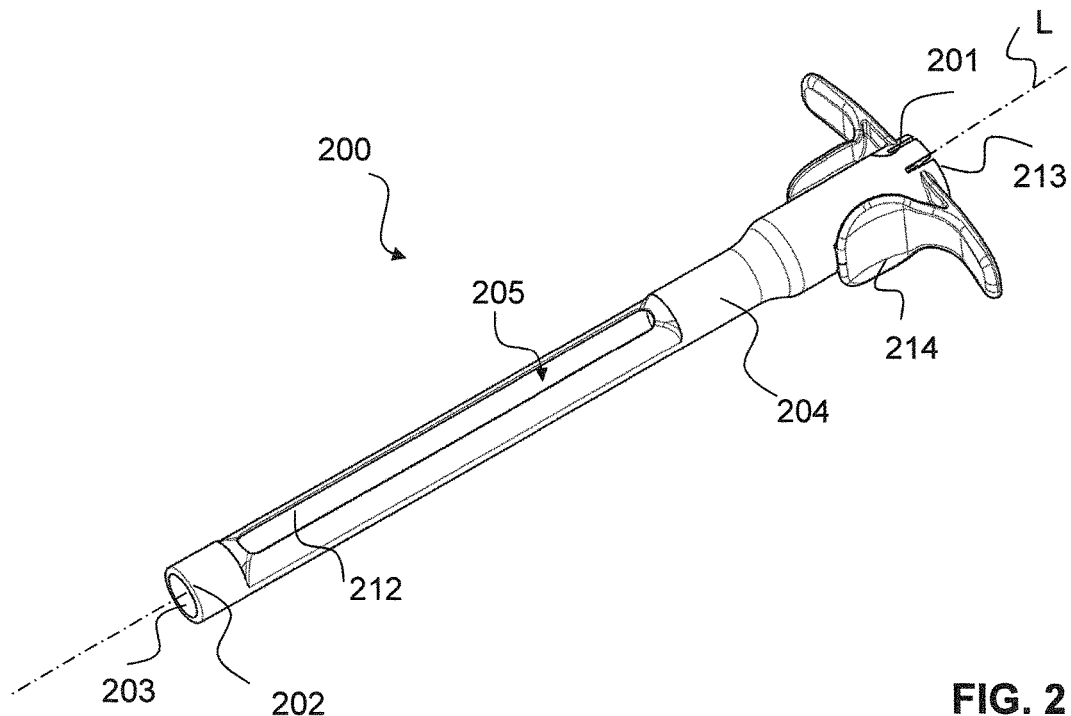
FIG. 2 shows a perspective view of the housing from FIG. 1.
Figure 3:
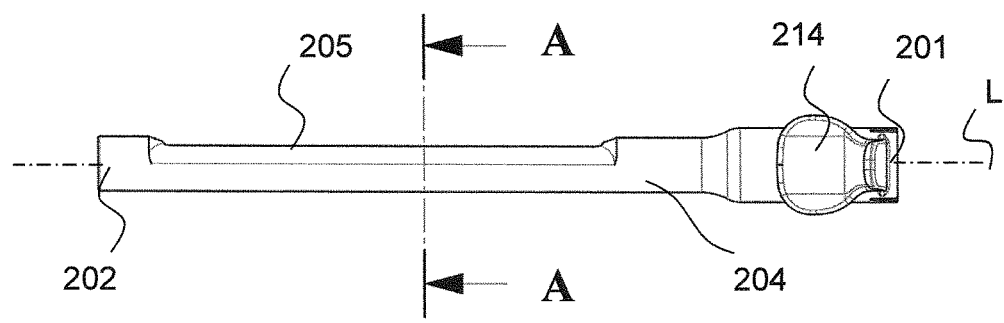
FIG. 3 shows a side view of the housing from FIG. 2.
Figure 4:
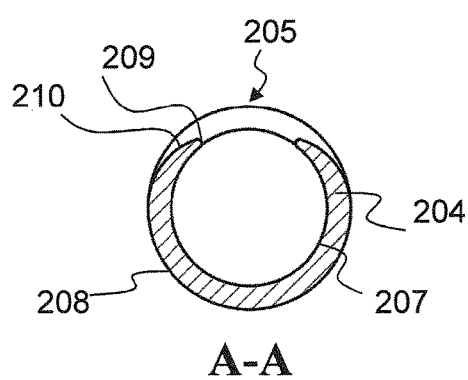
FIG. 4 shows a cross-section through the housing from FIG. 3 in the plane A-A from FIG. 3.

The housing 200 is shown separately in FIGS. 2-4. Said housing comprises a peripheral housing wall (jacket wall) 204 which delimits an inner housing chamber 212 and defines a proximal housing inlet opening 213 and a distal housing outlet opening 203. In the region of the proximal housing end 201, the housing 200 has an expanded region on which a handle 214 in the form of two grip wings is formed. Adjoining the proximal expanded region in the distal direction is a cylindrical region which extends up to the distal housing end 203. In this cylindrical region, an elongate, lateral cutout 205 (i.e., a window) is formed in the housing wall 204, which is delimited in the circumferential direction by two parallel edges extending in parallel to the longitudinal axis L.

The housing wall 204 defines an inner housing lateral face 207 and an outer housing lateral face 208. The wall thickness of the housing wall 204 decreases continuously in the circumferential direction toward the lateral cutout 205. The inner housing lateral face 207 and the outer housing lateral face 208 enclose an acute angle with respect to one another in this region in a cutting plane perpendicular to the circumferential direction and meet at a scraping edge 209. The function of this scraping edge will be described in greater detail in the following in conjunction with FIG. 11.

Figure 5:
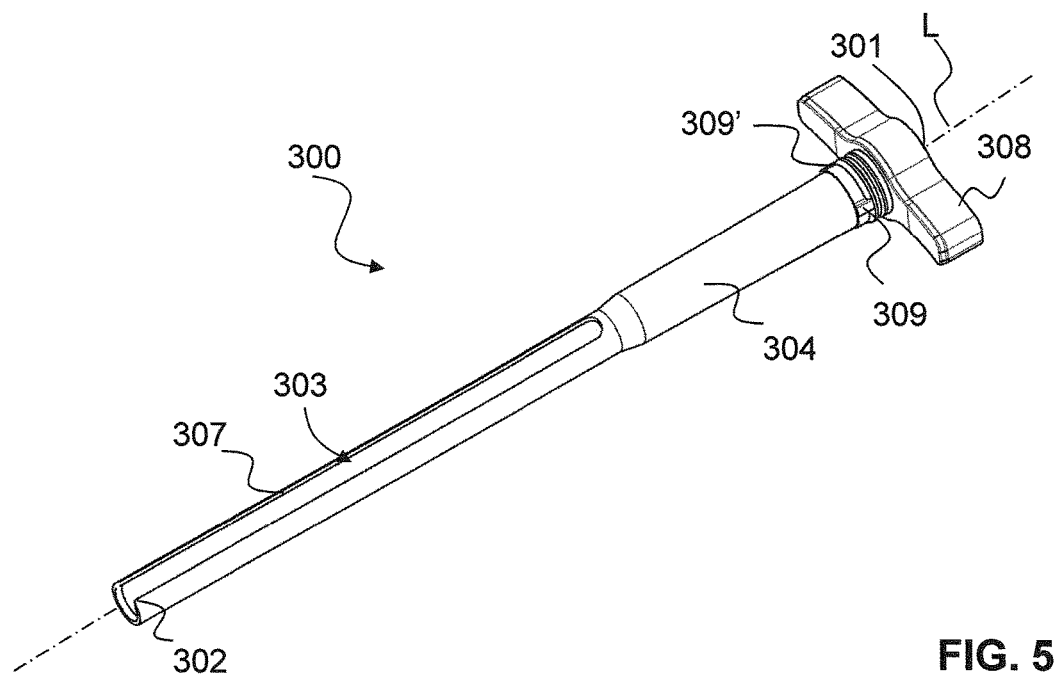
FIG. 5 shows a perspective view of the container insert from FIG. 1.
Figure 6:
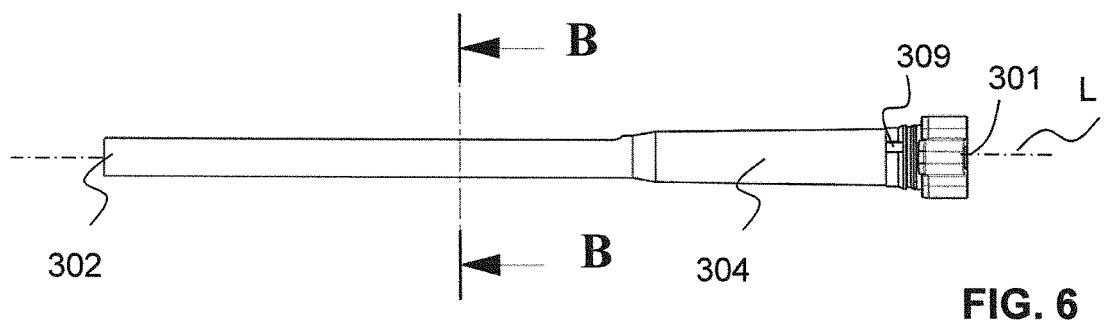
FIG. 6 shows a side view of the container insert from FIG. 5.
Figure 7:
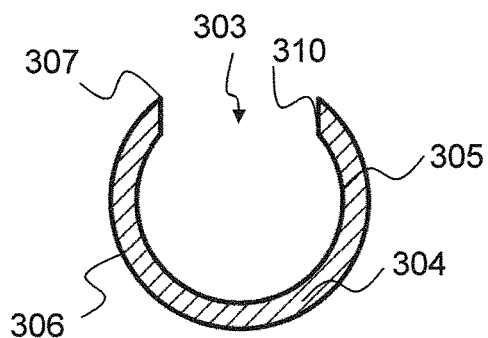
FIG. 7 shows a cross-section through the container insert from FIG. 6 in the plane B-B from FIG. 6.

The container insert 300 is shown separately in FIGS. 5-7. Said container insert comprises a container wall 304, an open proximal container end 301, and an open distal container end 302. The container wall 304 has a proximally located, expanded region adjoined by a narrower cylindrical region. In this cylindrical region, a lateral container opening 303 is formed in the container wall 304. The lateral container opening 303 extends continuously in parallel to the longitudinal axis L up to the distal container end 302 without a region of the container wall 304 adjoining the lateral container opening 303 in the distal direction along the longitudinal axis L.

The container wall 304 defines an inner container lateral face 305 and an outer container lateral face 306. These lateral faces are each connected, on both sides of the lateral container opening, by a shearing surface 310, wherein each of these shearing surfaces can be considered to be part of the inner container lateral face 305 that is slanted with respect to the circumferential direction. The shearing surfaces 310 and the outer container lateral face 306 meet at one shearing edge 307 in each case. The container wall 304 therefore tapers in the circumferential direction toward the lateral container opening 303 in such a way that said wall forms a blade-like shearing edge 307 in each case. In this case, the particular shearing surface 310 (as part of the inner container lateral face 305) and the outer container lateral face 306 enclose an acute angle with respect to one another in a cutting plane perpendicular to the circumferential direction. The shearing surfaces 310 and shearing edges 307 are described in greater detail in the following in conjunction with FIG. 11.

The hollow space delimited by the inner container lateral face 306 has an open cross-section which expands very slightly in the distal direction, as will be described in greater detail in conjunction with FIGS. 28 to 38.

Two radially protruding cams 309, 309' which function as container rotation stops are formed at the proximal container end 301. This is described in greater detail in the following in conjunction with FIG. 12. In addition, a radially protruding twist handle 308, which facilitates a rotation of the container insert 300 in the housing 200, is formed at the proximal container end 301.

Figure 8:
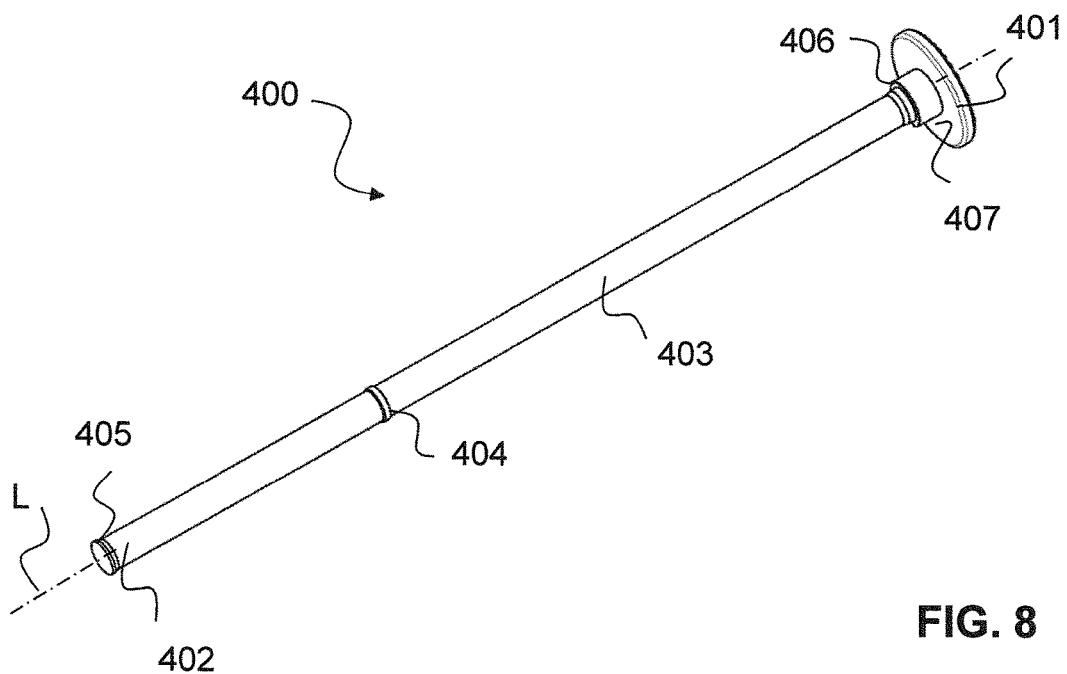
FIG. 8 shows a perspective view of the rod from FIG. 1.
Figure 9:
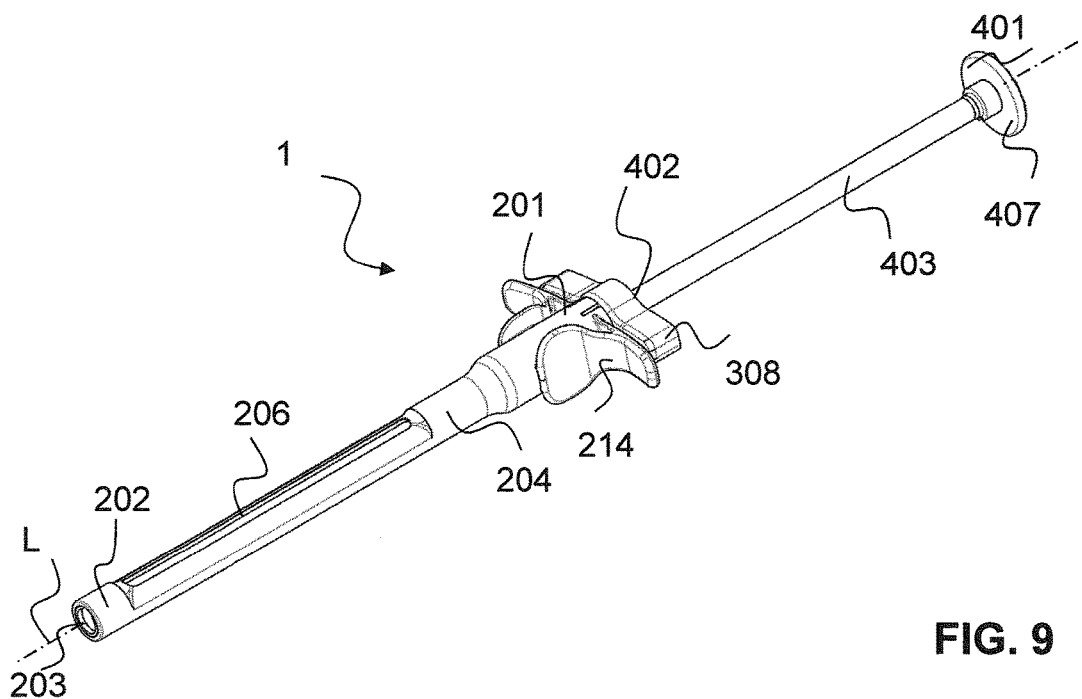
FIG. 9 shows a perspective view of the discharge device in a release position.
Figure 13:
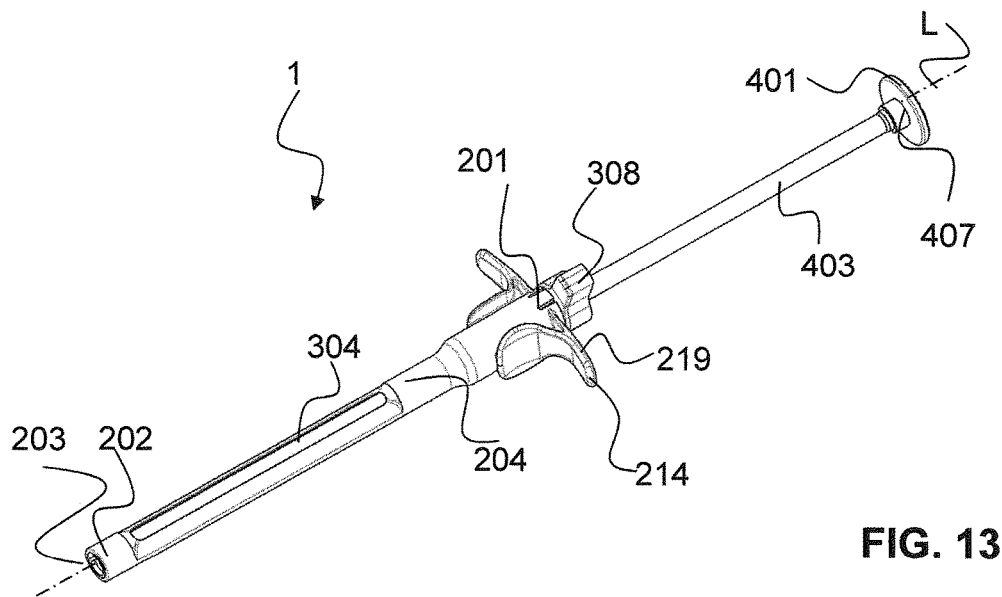
FIG. 13 shows a perspective view of the discharge device in a closed position.
Figure 14:
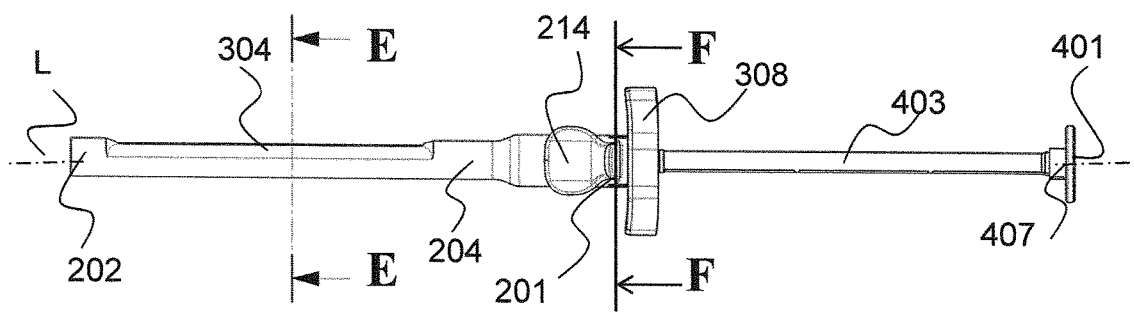
FIG. 14 shows a side view of the discharge device from FIG. 13.
Figures 15, 16:
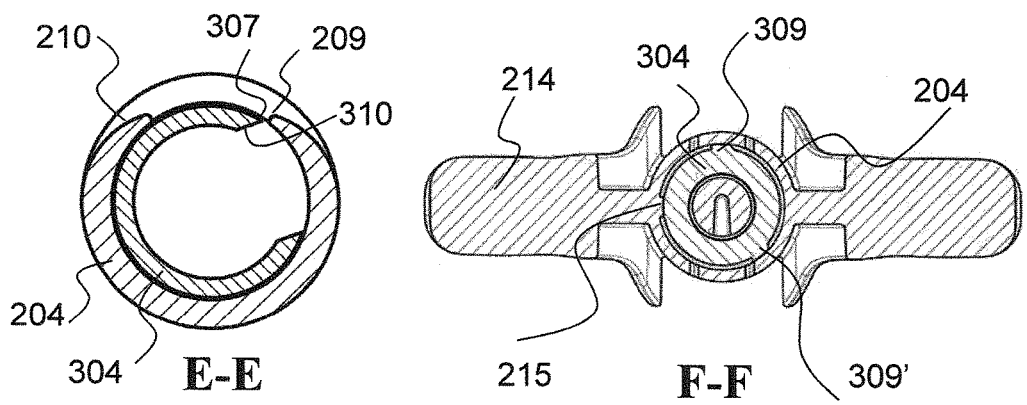
FIG. 15 shows a cross-section through the discharge device from FIG. 14 in the plane E-E from FIG. 14.
FIG. 16 shows a cross-section through the discharge device from FIG. 14 in the plane F-F from FIG. 14.
Figure 17:
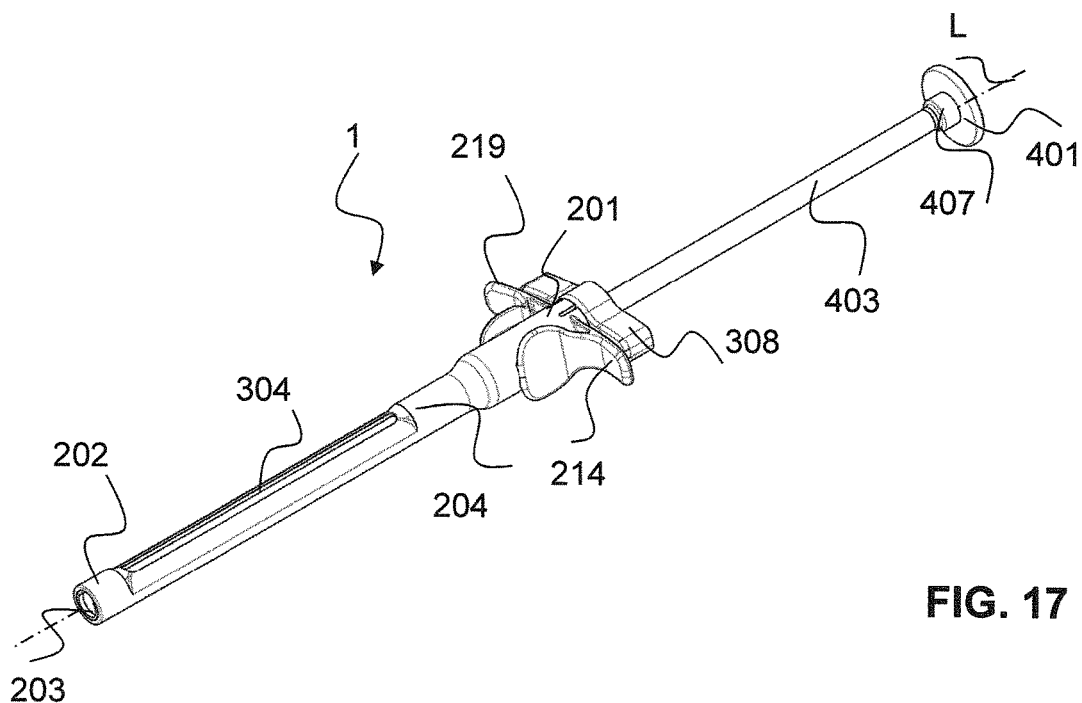
FIG. 17 shows a perspective view of the discharge device in an end state.
Figure 18:
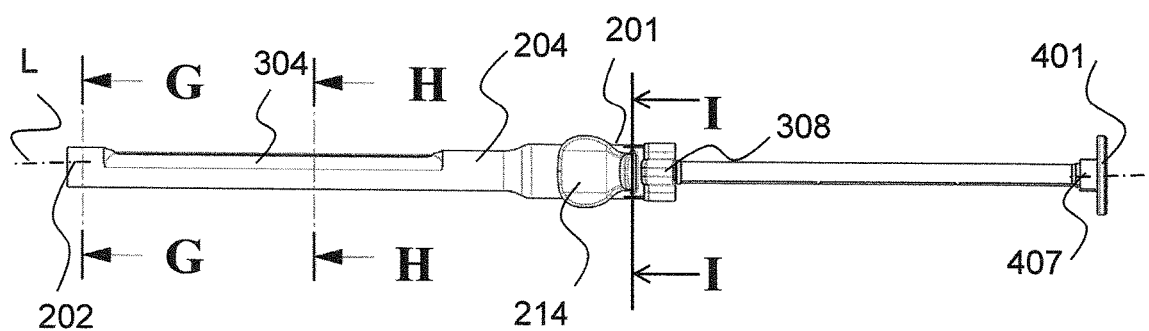
FIG. 18 shows a side view of the discharge device from FIG. 17.
Figure 19:
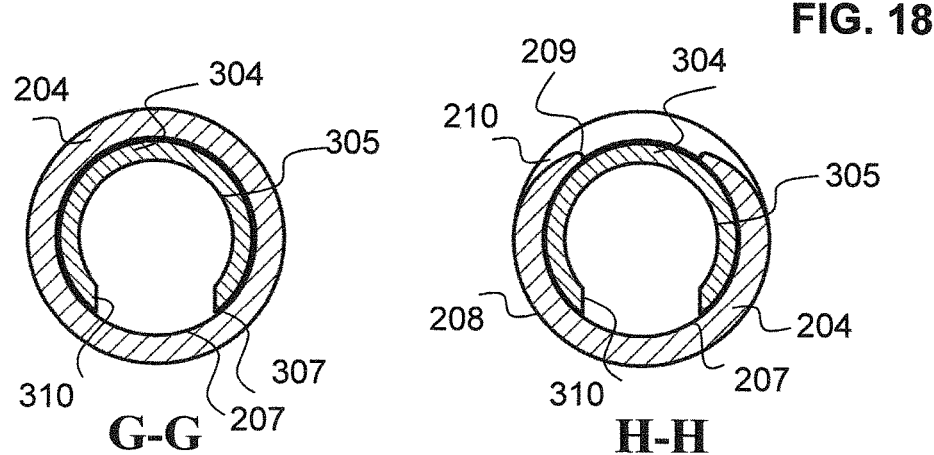
FIG. 19 shows a cross-section through the discharge device from FIG. 18 in the plane G-G and a cross-section through the discharge device from FIG. 18 in the plane H-H from FIG. 18.

The rod 400 is shown alone in FIG. 8. At its distal end 402, the rod 400 comprises a piston 405 which is proximally adjoined by a push rod 403. The piston 405 extends radially slightly beyond the push rod 403 in this case, i.e., said piston has a piston diameter which is larger than the rod diameter of the push rod 403. The properties of the piston 405 resulting therefrom are described in greater detail in FIGS. 28 to 33. At its proximal rod end 401, the push rod 403 is connected to a pressure plate 407 via a connecting piece 406. In this embodiment, the pressure plate 407 is a disk-shaped thumb rest, on which a user can apply manual pressure for discharging the mass out of the discharge device 1. The push rod 403 comprises a rod stop in the form of an annular ridge 404 encircling the push rod 403, the function of which will be described in greater detail in conjunction with FIG. 27.

FIGS. 9-12 show the discharge device in a release position (filling position). In this case, the container insert 300 has been slid through the proximal housing end 201 into the inner housing chamber 212 until the twist handle 308 of the container insert 300 rests against the proximal housing end 201, and the rod 400 has been slid via its distal rod end 402 into the open proximal container end 301 of the container insert 300. In this release position, the lateral container opening 303 in the container wall 304 is located directly below the lateral cutout 205 of the housing wall 204, such that the lateral container opening 303, together with the lateral cutout 205, defines a common filling opening 206 in the discharge device 1. The mass is now filled by a user into this filling opening 206, i.e., through the lateral cutout 205 of the housing 200 and the lateral filling opening 303 of the container insert 300, into the interior of the container insert 300. This can take place manually and/or with the aid of a tool, e.g., a spatula.

It becomes evident from FIG. 11 in particular that the outer container lateral face 306 of the container wall 304 is in contact with the inner housing lateral face 207 of the housing wall 204, and, in the release position, the shearing edges 307 of the container insert are situated directly adjacent to the scraping edges 209 of the housing. In order to fill the container insert 300, a mass, e.g., a bone replacement material, can be spread over the lateral cutout 205 of the housing 200 along a scraping direction extending transversely to the longitudinal axis L. The scraping edge 209 functions as a filling aid in this case and makes it easier to scrape off the mass. The mass is sheared off toward the inside by means of the shearing edge 307 and thereby enters the interior of the container insert 300.

As described above, the wall thickness of the housing wall 204 continuously decreases toward the lateral cutout 205 on the outside in the circumferential direction over an angular range a in order to form the scraping edge 209. This angular range a is approximately 35° in this case. The continuous decrease in the wall thickness toward the lateral cutout 205 across a relatively large angular range ensures that the outer housing lateral face 208 curves continuously outwardly with respect to the circumferential direction away from the scraping edge 209 without a normal vector N on the outer housing lateral face 208 having a directional component which extends in the direction of a radial plane P extending centrally through the lateral cutout 205. A funnel effect is avoided as a result. In the present case, the radial plane P is a plane of symmetry of the housing 200, and the housing 200 is designed with mirror symmetry with respect to this radial plane P.

The cooperation of the radially protruding cams 309, 309', each of which forms a container rotation stop, with a cam 215, which is formed so as to be complementary thereto on the housing and which forms a housing rotation stop, is illustrated in FIG. 12. In the release position, the cam 309 strikes the cam 215 in the circumferential direction and thereby prevents further rotation of the container insert 300 in the housing 200 in the counterclockwise direction.

FIGS. 13-16 illustrate an intermediate position of the discharge device, which lies between the release position and the closed position. In this intermediate position, the discharge device 1 was filled with the mass, initially in its release position, and the container insert 300 was subsequently rotated in the housing 200 about the longitudinal axis L to the extent that the scraping edge 209 on the one side of the lateral cutout of the housing is in contact with the shearing edge 307 on the opposite side of the lateral container opening. In this case, the shearing surface 310—which extends diagonally with respect to the circumferential direction—on the shearing edge 307 causes parts of the mass that are still located in the region of the scraping edge 209 to be sheared off by the shearing edge 307 and to be pushed in the direction of the interior of the container insert. Due to this shearing effect, the risk that, e.g., bone fragments, will become lodged between the container wall 304 and the housing wall 204 is reduced.

FIGS. 17-20 illustrate the closed position of the discharge device. In this closed position, the container insert 300 was rotated further, starting from the intermediate position, such that the container opening 303 in the container insert 300 is now located on an opposite side of the lateral cutout 205 of the housing 200 and, as a result, is completely covered by the housing wall 204. In other words, the filling opening 206 is now securely closed, and the discharge device 1 is ready for discharge.

Figure 20:
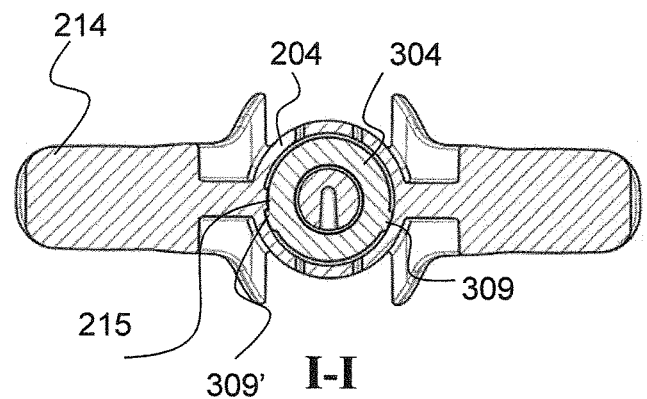
FIG. 20 shows a cross-section through the discharge device from FIG. 18 in the plane I-I from FIG. 18.

FIG. 20 illustrates how, in this position, the cam 309' functioning as a container rotation stop strikes, in the circumferential direction, the cam 215 functioning as the housing rotation stop and thereby prevents the further rotation of the container insert 200 in the clockwise direction past the closed position.

Figure 21:
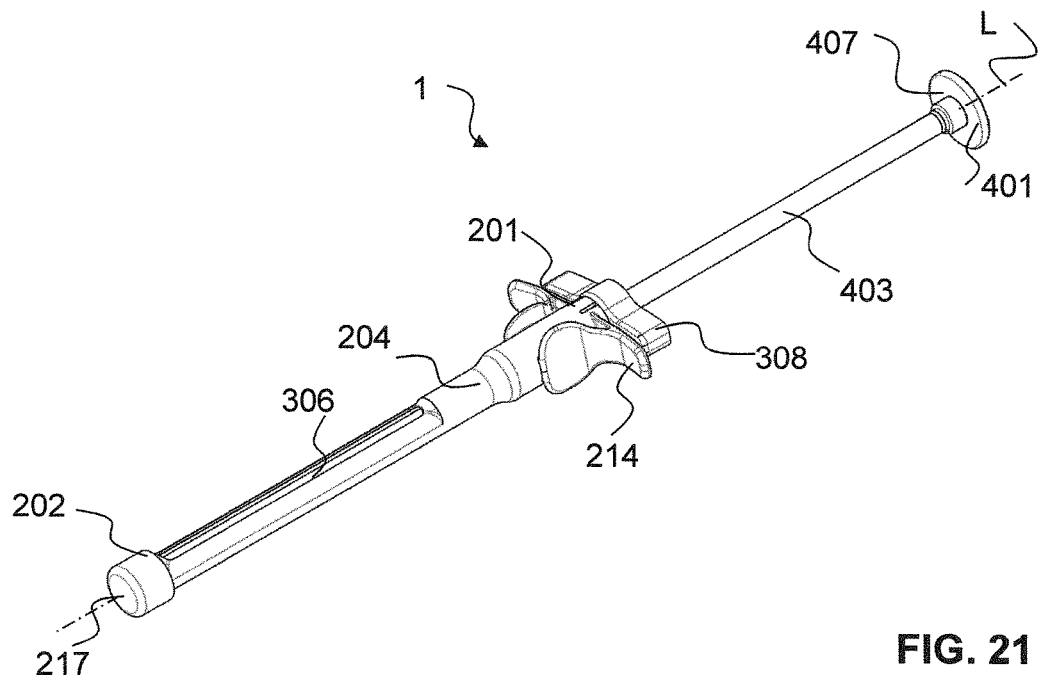
FIG. 21 shows a perspective view of a second exemplary embodiment of a discharge device.
Figure 22:
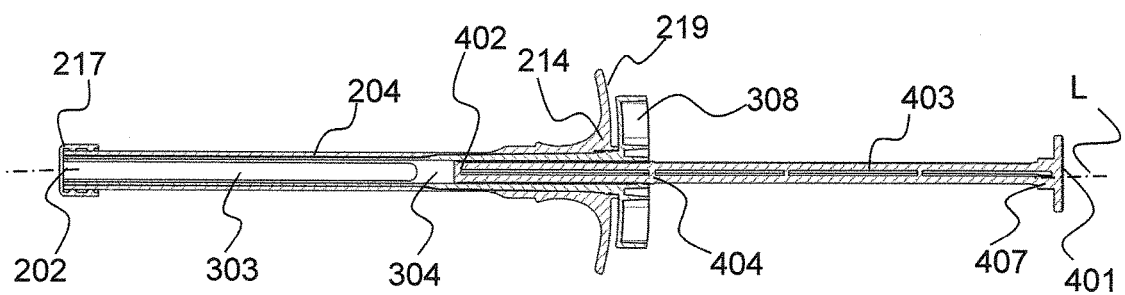
FIG. 22 shows a cross-section along a longitudinal axis through the discharge device from FIG. 21.
Figure 23:
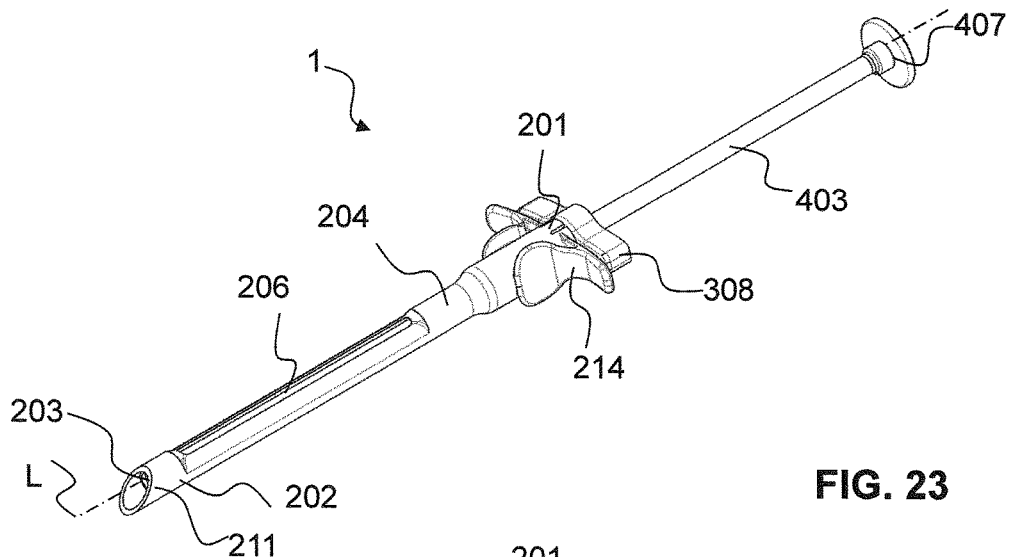
FIG. 23 shows a perspective view of a third exemplary embodiment of a discharge device.
Figure 24:
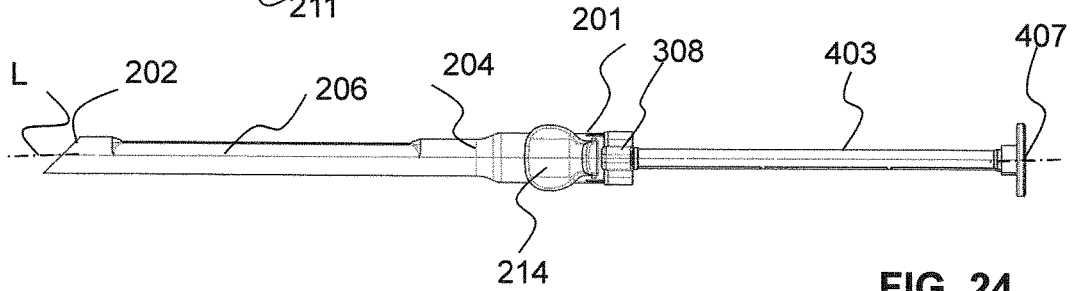
FIG. 24 shows a side view of the discharge device according to FIG. 23.
Figure 25:
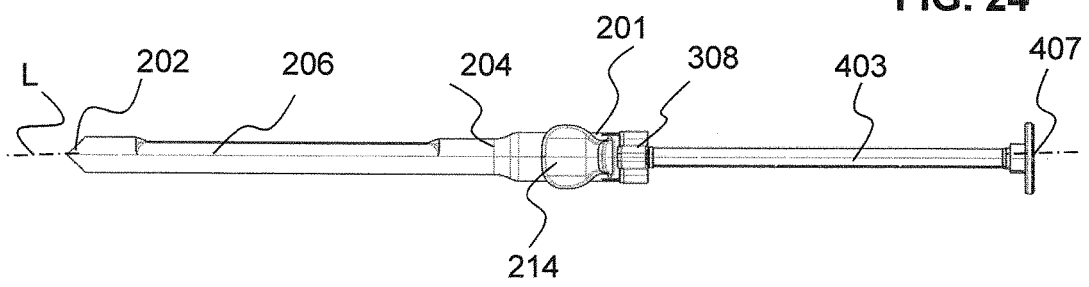
FIG. 25 shows a side view of a fourth exemplary embodiment of a discharge device.

FIG. 21 shows a discharge device according to a second embodiment. This second embodiment largely corresponds to the first embodiment but comprises a removable closure 217 in the form of a closure cap. The closure cap 217 is designed as a screw cap in this case. Said cap closes the housing outlet opening 203 by way of an internal thread—which is formed on an inner side of the closure cap—having threaded engagement with a corresponding outer thread which is formed on the outer housing lateral face 208 on the distal housing end 202.

This embodiment is advantageous primarily when the container insert 300, which was prefilled with a component of the mass to be discharged (e.g., a powder), has been slid into the housing 200. In the closed position, this component is completely enclosed in the discharge device. In order to now add a further component (e.g., a liquid component such as blood, blood plasma, or aspirated bone marrow), a user grips the twist handle 308 of the container insert 300 and rotates said handle in such a way that the discharge device moves into the release position. The user can now fill the second component (e.g., wet the powder) therein and transfer the discharge device 1 into the closed position again by rotating the container insert 300 in the housing 200. The housing outlet opening 203 is subsequently exposed by removing the closure cap 217, and therefore the mass, which has been made available in this way, can be discharged by advancing the rod 400.

FIGS. 23 to 26 show a third and a fourth embodiment of a discharge device. These embodiments, in turn, largely correspond to the first embodiment, wherein the distal housing end 202 has a different design in each case, however. In the third embodiment according to FIGS. 23 and 24, the distal housing end extends diagonally with respect to the longitudinal axis L. In the fourth embodiment according to FIGS. 25 and 25, adjoining the distal housing end is a deflector 211 which is curved in the distal direction toward the central longitudinal axis L along the distal direction. Due to these embodiments, it is easier to discharge the mass toward one side.

Figure 26:
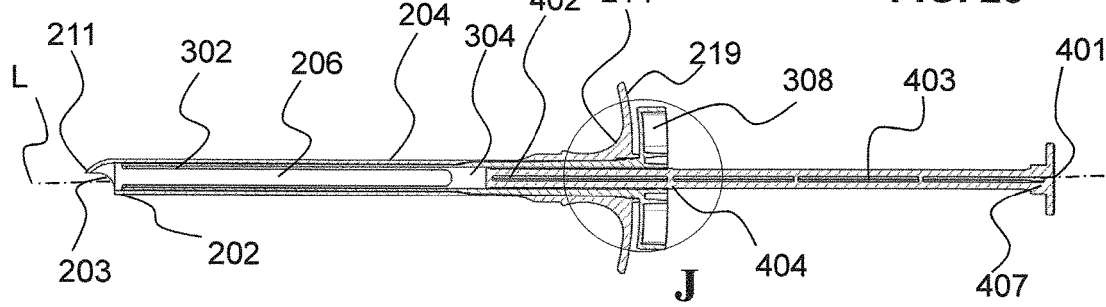
FIG. 26 shows a cross-section along the longitudinal axis through the discharge device according to FIG. 25.
Figure 27:
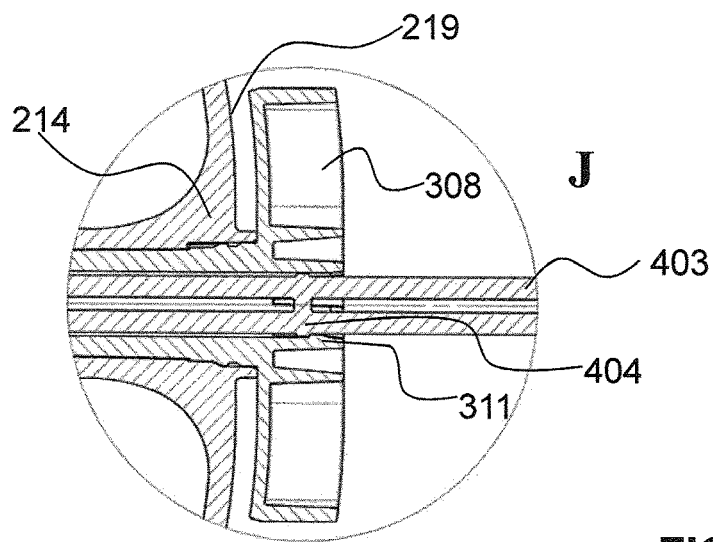
FIG. 27 shows a detailed view of the region J from FIG. 26 with the rod locked in position.

FIG. 27 shows a detailed view of the region J of FIG. 26, wherein the rod 400, via its rod stop 404 in the form of an annular ridge, strikes a container stop 311 in the form of a detent projection in the open proximal container end 301 in such a way that a displacement of the rod 400 along the proximal direction through the proximal housing end 201 out of the container insert 300 is prevented. As a result, the rod 400 can be prevented from falling out of the discharge device.

Figure 28:
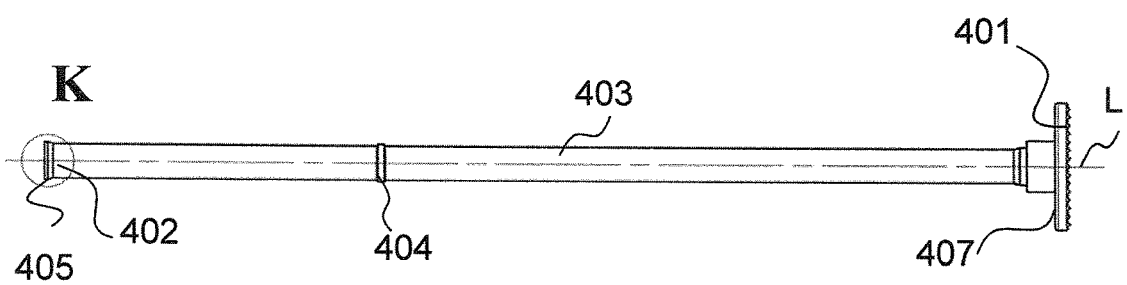
FIG. 28 shows a side view of the rod from FIG. 1.
Figure 29:
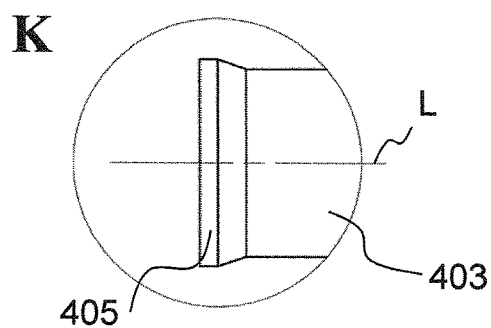
FIG. 29 shows a detailed view of the region K from FIG. 28.

FIGS. 28 and 29 illustrate the piston 400 according to the first embodiment, wherein the properties of the piston 405, which extends radially beyond the push rod 403, shall now be illustrated in particular. The piston 405 defines a piston diameter, while the push rod 403 defines a smaller rod diameter. The transition between the piston and the push rod takes place via a conical ramp.

FIGS. 30 to 33 illustrate a discharge device 1 according to the first embodiment, the container insert 300 of which continuously expands on the inside in the distal direction. Both the outer container lateral face 306 and the push rod 403 have a cylindrical shape having a constant diameter in each case, while the inner container lateral face 305 defines an inner container diameter which continuously increases along the longitudinal axis L in the distal direction. As the advance of the rod 400 in the container insert 300 increases, the radial spacing of the push rod 403 from the inner container lateral face 305 therefore becomes increasingly greater.

Figure 30:
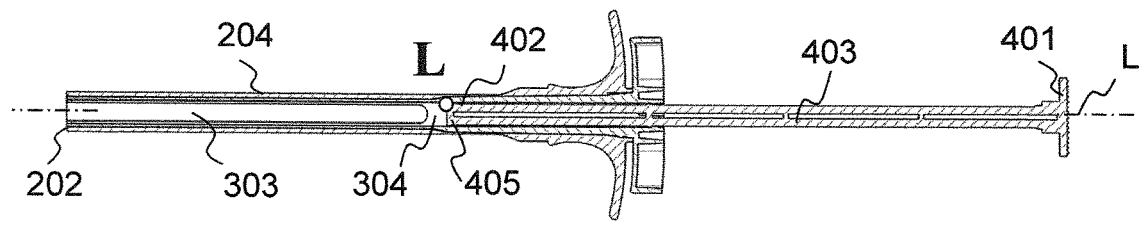
FIG. 30 shows a cross-section along the longitudinal axis through the discharge device from FIG. 9.
Figure 31:
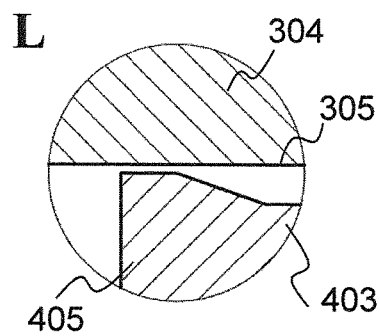
FIG. 31 shows a detailed view of the region L from FIG. 30.
Figure 32:
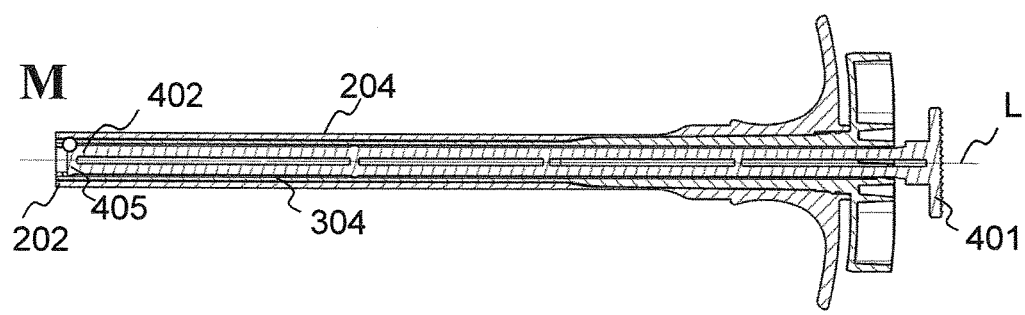
FIG. 32 shows a cross-section along the longitudinal axis through the discharge device from FIG. 9, with the rod having been advanced.
Figure 33:
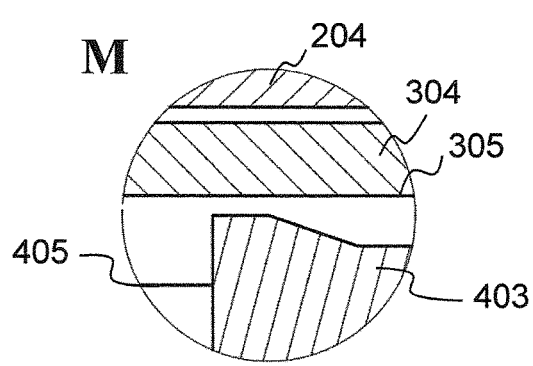
FIG. 33 shows a detailed view of the region M from FIG. 32.
Figure 34:
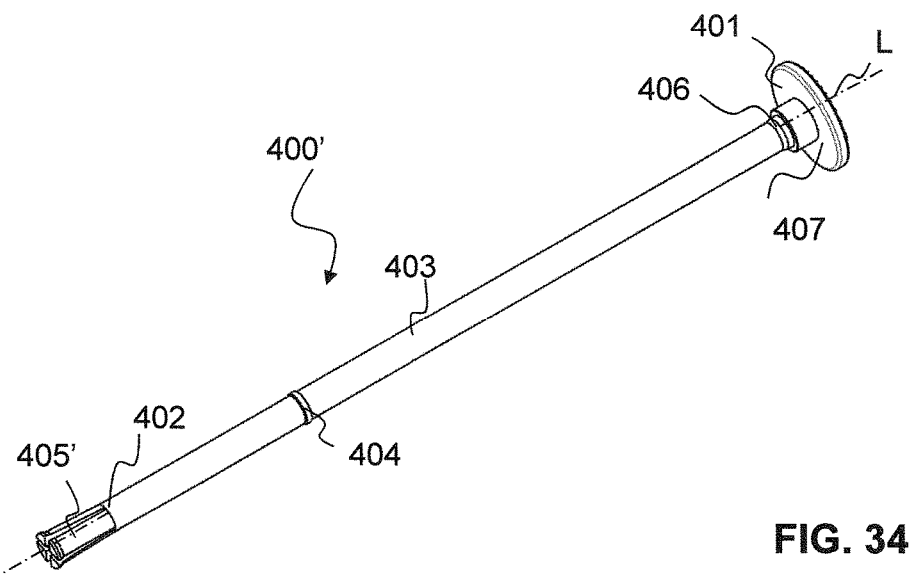
FIG. 34 shows a perspective view of a rod according to a fifth exemplary embodiment of the invention.
Figure 35:
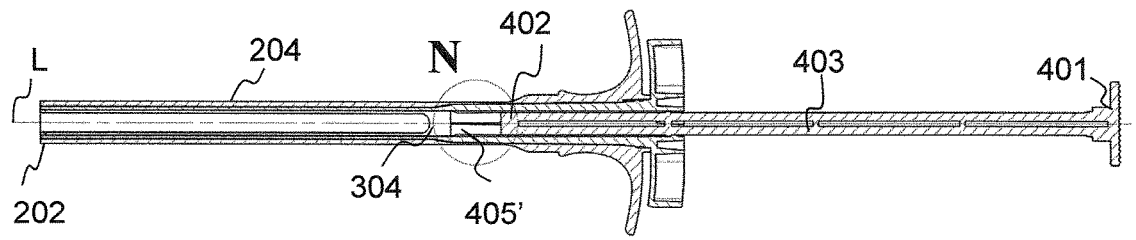
FIG. 35 shows a cross-section along the longitudinal axis through a discharge device comprising a rod according to FIG. 34.
Figure 36:
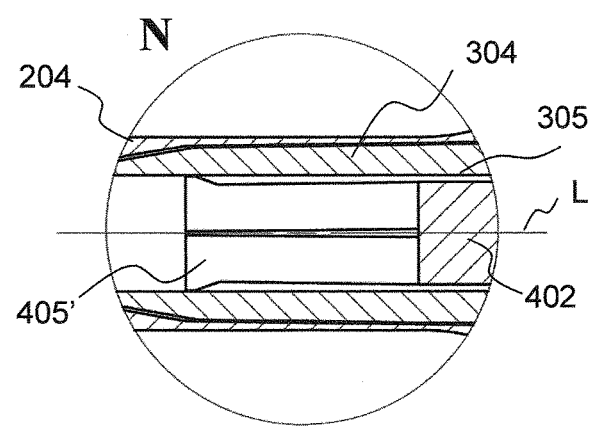
FIG. 36 shows a detailed view of the region N from FIG. 35.
Figure 37:
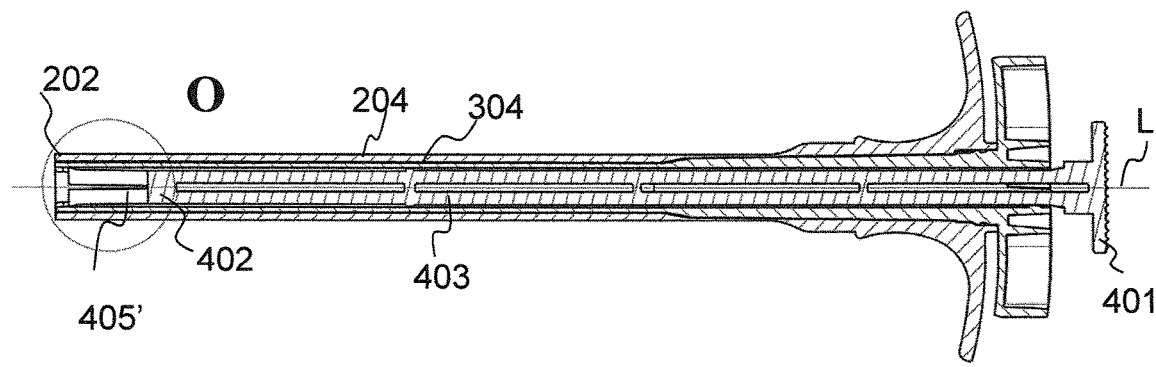
FIG. 37 shows a cross-section along the longitudinal axis through the discharge device from FIG. 35, with the rod having been advanced.
Figure 38:
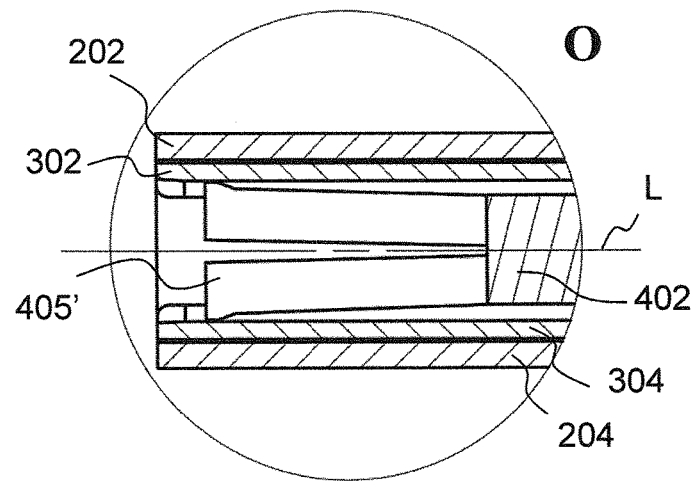
FIG. 38 shows a detailed view of the region O from FIG. 37.

FIG. 30 shows the discharge device 1 comprising a rod 400 accommodated therein, the distal rod end 402 of which is located in the region of the proximal container end 302. FIG. 31 shows a detailed view of the region L of FIG. 30, which shows that the outer circumferential surface of the piston 405 is located in direct proximity to the inner container lateral face 305 in this case, although a narrow gap is formed therebetween. Said gap is adjoined, in the proximal direction, by a larger gap between the outer lateral face of the push rod 403 and the inner container lateral face 305. FIGS. 32 and 33 show the discharge device 1 comprising a rod 400 accommodated therein, wherein the rod 400 has been advanced in the distal direction and is now located with its distal rod end 402 in the region of the distal housing end 202 and the container end 302. Since the inner container lateral face 305 defines a container diameter which increasingly enlarges along the distal direction, the gap between the outer lateral face of the piston 405 or the outer lateral face of the push rod 403 and the inner container lateral face 305 also increases in a corresponding manner. Due to this gap, which increases in the distal direction, a jamming of the rod 400 can be avoided if the mass enters the gap between the piston 405 and the inner container lateral face 305 or even passes by the piston 405 and enters the region of the push rod 403. In this case, it suffices when the diameter of the container expands only very slightly, e.g., by less than one-tenth of a millimeter per centimeter of length (i.e., by less than 1 percent).

A fifth embodiment of the invention is illustrated in FIGS. 34 to 38. This embodiment corresponds to the first embodiment, although the rod 400' comprises, at its distal rod end, a piston 405' having two intersecting slots (indentations), wherein the slots extend radially through the piston 405' and are open in the distal direction. These slots are positioned perpendicularly to one another and subdivide the piston into four identical segments in this case. These segments can deflect radially inward, in the direction of the longitudinal axis, when a radial forces acts on said segments. This makes it possible for the piston 405' to expand radially or compress radially along the radial direction when said piston is guided through a container having a changeable open cross-section.

For this purpose, FIGS. 35 to 38, similarly to FIGS. 30 to 33, illustrate the use of this rod 400' in a discharge device 1, the container insert 300 of which continuously conically expands on the inside in the distal direction. The slotted piston 405' has a smaller radial expansion and a smaller circumference in the proximal region of the container insert 300, with a smaller inner container diameter, than in the distal region with a larger inner container diameter, since the segments of the piston 405' increasingly spread apart in a resilient manner as the inner container diameter increases. In this case, the slotted piston 405' ensures that the mass to be discharged can be efficiently and completely discharged even in the case of a relatively greatly distally expanding container insert 300.

LIST OF REFERENCE NUMBERS 1 discharge device
200 housing
201 proximal housing end
202 distal housing end
203 housing outlet opening
204 housing wall
205 lateral cutout
206 filling opening
207 inner housing lateral face
208 outer housing lateral face
209 scraping edge
210 scraping surface
211 deflector
212 inner housing chamber
213 housing inlet opening
214 handle
215 housing rotation stop
216 grip surface
217 closure
300 container insert
301 proximal container end
302 distal container end
303 lateral container opening
304 container wall
305 inner container lateral face
306 outer container lateral face
307 shearing edge
308 twist handle
309, 309' container rotation stop
310 shearing surface
311 container stop
400, 400' rod
401 proximal rod end
402 distal rod end
403 push rod
404 rod stop
405, 405' piston
406 connecting piece
407 pressure plate
500 functional element
L longitudinal axis
P radial plane
N normal vector

The invention claimed is:

1. A discharge device for discharging a mass, comprising:
a housing having a peripheral housing wall, an open proximal housing end, and an open distal housing end, wherein a lateral cutout is formed in the housing wall;
a piston; and
a container insert, which is situated in the housing and comprises a peripheral container wall, an open proximal container end, and a distal container end, wherein a lateral container opening is formed in the container wall, and wherein the container insert can be rotated about a longitudinal axis relative to the housing between a closed position, in which the housing wall closes the lateral container opening, and a release position, in which the lateral cutout releases the lateral container opening,
wherein the lateral container opening extends continuously in an axial direction up to the distal container end without a region of the container wall adjoining the lateral container opening in a distal direction along the longitudinal axis, and
wherein the piston is displaceable in the container insert along the longitudinal axis.

2. A discharge device for discharging a mass, comprising:
a housing having a peripheral housing wall, an open proximal housing end, and an open distal housing end, wherein a lateral cutout is formed in the housing wall; and
a container insert, which is situated in the housing and comprises a peripheral container wall, an open proximal container end, and a distal container end,
wherein a lateral container opening is formed in the container wall, and
wherein the container insert can be rotated about a longitudinal axis relative to the housing between a closed position, in which the housing wall closes the lateral container opening, and a release position, in which the lateral cutout releases the lateral container opening, wherein the housing wall has a wall thickness in the region of the lateral cutout, which continuously decreases in the circumferential direction toward the lateral cutout through an angular range which is at least 10°.

3. The discharge device as claimed in claim 2, wherein the wall thickness of the housing wall decreases in the circumferential direction toward the lateral cutout in such a way that the housing wall forms a scraping edge on the lateral cutout.

4. The discharge device as claimed in claim 3, wherein the container wall tapers in the circumferential direction toward the lateral container opening in such a way that said wall forms a blade-like shearing edge adjacent to the housing wall, and wherein the scraping edge and the shearing edge adjoin one another in the release position.

5. A discharge device for discharging a mass, comprising:
a housing having a peripheral housing wall, an open proximal housing end, and an open distal housing end, wherein a lateral cutout is formed in the housing wall; and
a container insert, which is situated in the housing and comprises a peripheral container wall, an open proximal container end, and a distal container end,
wherein a lateral container opening is formed in the container wall,
wherein the container insert can be rotated about a longitudinal axis relative to the housing between a closed position, in which the housing wall closes the lateral container opening, and a release position, in which the lateral cutout releases the lateral container opening, and
wherein the container insert has an open container cross-section which continuously increases in a distal direction along the longitudinal axis across an axial range.

6. The discharge device as claimed in claim 5, wherein the axial range, across which the container cross-section continuously increases, extends from a proximal end of the container opening up to the distal container end.

7. The discharge device as claimed in claim 1,
wherein the piston defines a piston diameter,
wherein the piston is connected to a push rod,
wherein the push rod defines a rod diameter, and
wherein the piston diameter is larger than the rod diameter.

8. The discharge device as claimed in claim 1, wherein the piston is slotted in such a way that said piston is capable of expanding radially.

9. The discharged device as claimed in claim 1, wherein a deflector is formed on the distal housing end, which adjoins the distal container end in the distal direction and is curved along the distal direction toward the central longitudinal axis.

10. The discharge device as claimed in claim 1, wherein at least one container rotation stop is formed on the container insert, and at least one housing rotation stop is formed on the housing, wherein the container rotation stop is formed so as to be contradirectional to the housing rotation stop, and wherein the container rotation stop and the housing rotation stop are arranged in such a way that the container rotation stop and the housing rotation stop strike one another at least one of during a rotation of the container insert in the housing in the direction of the release position and during an opposing rotation in the direction of the closed position.

11. The discharge device as claimed in claim 1, wherein the container insert is prefilled with a mass, and wherein the discharge device comprises a removable closure which closes a housing outlet opening.

12. A method of providing a mass to be discharged in a discharge device which comprises a housing having a housing wall and a lateral cutout formed therein, and a container insert, which is rotatably situated in the housing and comprises a container wall and a lateral container opening formed therein, wherein the container insert is prefilled with a first component of the mass, and a removable closure closes the discharge device, and wherein the method comprises the following steps of:
rotating the container insert relative to the housing about the longitudinal axis, such that the lateral cutout releases the lateral container opening;
adding a second component of the mass through the lateral cutout and through the lateral container opening to the first component in the container insert;
rotating the container insert relative to the housing about the longitudinal axis, such that the housing wall closes the lateral container opening; and
removing the closure.

13. The discharge device as claimed in claim 2, which also comprises a piston which is displaceable in the container insert along the longitudinal axis.

14. The discharge device as claimed in claim 13,
wherein the piston defines a piston diameter,
wherein the piston is connected to a push rod,
wherein the push rod defines a rod diameter, and
wherein the piston diameter is larger than the rod diameter.

15. The discharge device as claimed in claim 13, wherein the piston is slotted in such a way that said piston is capable of expanding radially.

16. The discharged device as claimed in claim 2, wherein a deflector is formed on the distal housing end, which adjoins the distal container end in the distal direction and is curved along the distal direction toward the central longitudinal axis.

17. The discharge device as claimed in claim 2, wherein at least one container rotation stop is formed on the container insert, and at least one housing rotation stop is formed on the housing, wherein the container rotation stop is formed so as to be contradirectional to the housing rotation stop, and wherein the container rotation stop and the housing rotation stop are arranged in such a way that the container rotation stop and the housing rotation stop strike one another at least one of during a rotation of the container insert in the housing in the direction of the release position and during an opposing rotation in the direction of the closed position.

18. The discharge device as claimed in claim 2, wherein the container insert is prefilled with a mass, and wherein the discharge device comprises a removable closure which closes a housing outlet opening.

19. The discharge device as claimed in claim 5, which also comprises a piston which is displaceable in the container insert along the longitudinal axis.

20. The discharge device as claimed in claim 19,
wherein the piston defines a piston diameter,
wherein the piston is connected to a push rod,
wherein the push rod defines a rod diameter, and
wherein the piston diameter is larger than the rod diameter.

21. The discharge device as claimed in claim 19, wherein the piston is slotted in such a way that said piston is capable of expanding radially.

22. The discharged device as claimed in claim 5, wherein a deflector is formed on the distal housing end, which adjoins the distal container end in the distal direction and is curved along the distal direction toward the central longitudinal axis.

23. The discharge device as claimed in claim 5, wherein at least one container rotation stop is formed on the container insert, and at least one housing rotation stop is formed on the housing, wherein the container rotation stop is formed so as to be contradirectional to the housing rotation stop, and wherein the container rotation stop and the housing rotation stop are arranged in such a way that the container rotation stop and the housing rotation stop strike one another at least one of during a rotation of the container insert in the housing in the direction of the release position and during an opposing rotation in the direction of the closed position.

24. The discharge device as claimed in claim 5, wherein the container insert is prefilled with a mass, and wherein the discharge device comprises a removable closure which closes a housing outlet opening.

\* \* \* \* \*